United States Patent [19]
White

[11] Patent Number: 5,684,530
[45] Date of Patent: *Nov. 4, 1997

[54] CONTINUOUS DIFFUSE ILLUMINATION METHOD AND APPARATUS

[75] Inventor: Timothy Peter White, New Boston, N.H.

[73] Assignee: Northeast Robotics, Inc., Weare, N.H.

[*] Notice: The term of this patent shall not extend beyond the expiration date of Pat. No. 5,461,417.

[21] Appl. No.: 531,339

[22] Filed: Sep. 20, 1995

Related U.S. Application Data

[63] Continuation-in-part of Ser. No. 131,695, Oct. 5, 1993, Pat. No. 5,461,417, which is a continuation-in-part of Ser. No. 18,233, Feb. 16, 1993, abandoned.

[51] Int. Cl.$^6$ ............................................. H04N 7/18
[52] U.S. Cl. .......................... 348/131; 348/125; 348/126; 348/87; 348/92; 348/141
[58] Field of Search .......................... 348/131, 125, 348/126, 86, 87, 88, 133, 128, 92, 91; 382/141; H04N 7/18

[56] References Cited

U.S. PATENT DOCUMENTS

| | | | |
|---|---|---|---|
| 3,322,487 | 5/1967 | Renner | 89/352 |
| 3,558,894 | 1/1971 | Odone | 261/350 |
| 4,067,026 | 1/1978 | Pappanikolaou | 77/354 |
| 4,139,306 | 2/1979 | Norton | 348/131 |
| 4,341,449 | 7/1982 | Iwata et al. | 396/61 |
| 4,677,473 | 6/1987 | Okamoto et al. | 348/131 |
| 4,816,686 | 3/1989 | Hara et al. | 348/126 |
| 4,965,665 | 10/1990 | Amir | 348/131 |
| 5,060,065 | 10/1991 | Wasserman | 348/131 |
| 5,064,291 | 11/1991 | Reiser | 348/131 |
| 5,172,005 | 12/1992 | Cochran et al. | 348/88 |
| 5,187,611 | 2/1993 | White et al. | 348/131 |
| 5,461,417 | 10/1995 | White et al. | 348/131 |

*Primary Examiner*—Tommy P. Chin
*Assistant Examiner*—Vu Le
*Attorney, Agent, or Firm*—Davis and Bujold

[57] ABSTRACT

The method and apparatus for providing an elongate linear continuous, uniformed, diffused lighting environment for use in conjunction with an electronic line scanner, a photocopier or a machine vision system, particularly for inspection and reproduction of specular surfaces such as documents or art work containing highly reflective areas on the surface thereof and other shiny surfaces. The linear illumination device includes at least one elongate source of light, illuminating a primary diffuser, to provide a primary diffused light source and a secondary elongate source of light illuminating a secondary diffuser to provide a secondary diffused light source supplied substantially along an observation plane of the illumination device. The two sources provide uniformly diffused lighting of an elongate strip of an object located at the object observing location to facilitate accurate viewing of a desired elongate portion of the object to be observed.

20 Claims, 11 Drawing Sheets

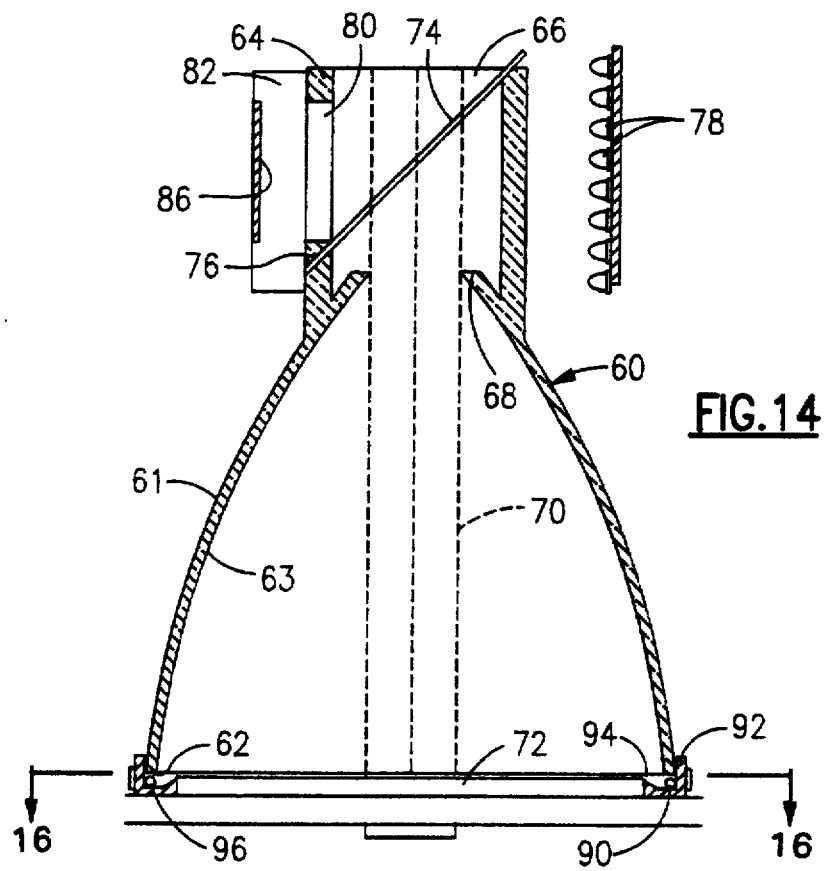
FIG. 14
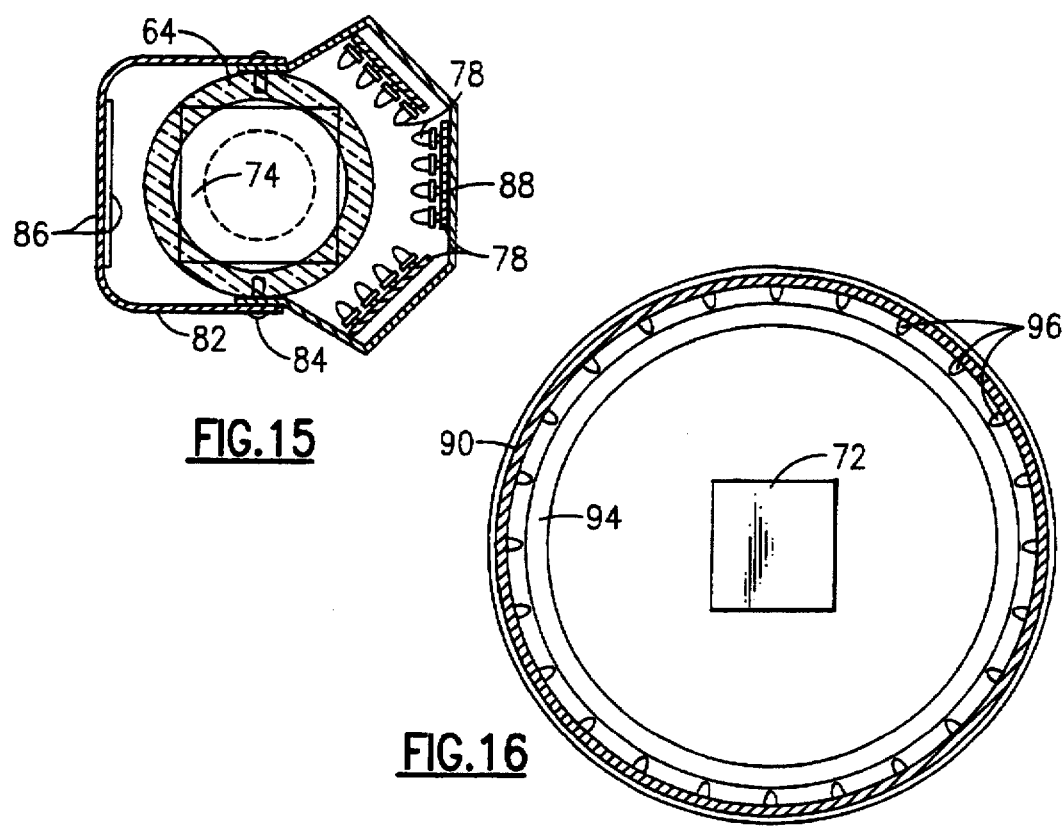
FIG. 15
FIG. 16

CONTINUOUS DIFFUSE ILLUMINATION METHOD AND APPARATUS

This is a continuation-in-part application of Ser. No. 08/131,695 filed Oct. 5, 1993, entitled "Continuous Diffuse Illumination Method and Apparatus" now U.S. Pat. No. 5,461,417, which is a continuation-in-part of Ser. No. 08/018,233, filed Feb. 16, 1993, entitled "Continuous Diffuse Lighting Fixture" now abandoned.

FIELD OF THE INVENTION

The invention pertains to a method and apparatus for permitting electronic machine vision of light reflecting objects wherein a true observation of the surface being viewed is obtained by masking potential reflections resulting along the observation axis/plane due to observation windows and cameras, or other non-illuminating discontinuities in the illumination environment. The invention also pertains to a method and apparatus for permitting such machine vision of an elongate linear portion of light reflecting objects.

DESCRIPTION OF THE RELATED ART

Electronic machine vision apparatus is commonly employed in conjunction with automatic machining, assembly and inspection apparatus, particularly of the robotics type. Television cameras are commonly employed to observe the object being machined, assembled, or inspected, and the signal received and transmitted by the camera can be compared to a standard signal or database to determine if the observed article is properly machined, oriented, or assembled. Also, machine vision apparatus is widely used in inspection and flaw detection applications whereby inconsistencies and imperfection in both hard and soft goods can be rapidly ascertained and adjustments or rejections instantaneously effected.

Machine vision apparatus detects abnormalities by comparing the signal generated by the camera with a predetermined signal indicating proper dimensions, appearance, orientation, or the like. In order to achieve consistent and accurate results when using machine vision apparatus employing electronic cameras, it is very important that consistent and uniform lighting of the observed object occur, as the lighting will seriously affect the vision signal generated and produce irregular signals even though no fault may exist in the object being observed other than it is not uniformly illuminated.

Illumination problems in machine vision applications are particularly present when the object being observed has a shiny specular surface. For instance, in the inspection of soldered circuits such as used with printed circuit boards the highly reflective nature and uneven surface geometry of the solder makes it very difficult to obtain an accurate electronic signal, and the same is true when machine vision inspecting ball bearings, reflective packaging, and other objects having shiny surfaces, particularly irregular shiny surfaces.

When utilizing machine vision techniques and apparatus in shiny surface applications, it is common to employ complicated lighting systems for illuminating the object being observed, and it is a purpose of such lighting systems to eliminate shadows, highlights, underlights, reflections and other lighting characteristics caused by shiny convex surface objects. Examples of complex lighting systems for use with machine vision apparatus are shown in U.S. Pat. Nos. 4,677,473; 4,882,498; 5,051,825; 5,060,065 and 5,072,127. While devices shown in these patents are capable of generating improved lighting characteristics, such devices do not eliminate erroneous signals resulting from the reflection of windows, openings or orifices defined in the lighting apparatus necessary to permit observation of the article being viewed, and such apparatus does not eliminate erroneous signals generated due to the reflection of cameras, openings or voids from specular objects.

Conventional illuminators for line-scanning image sensors, such as those currently used for printed web inspection or in common office copiers, use "dark field" illumination. That is, the light source is off to one side of the optical axis/plane so that there is no direct reflection of the light source into the imaging optics. While such illumination systems facilitate faithful reproduction of surfaces with diffuse reflecting characteristics, such as common office copy paper, for example, they fail to allow faithful reproduction of specular, i.e. "shiny" surfaces, whether flat or uneven. For example, a document or label including highly reflective metallic foil as part of its art work, when imaged using common off-axis/plane "dark field" illumination, will have the reflective foil reproduced as black, rather than light. This effect is exploited by the U.S. Mint in new large denomination bills to foil counterfeiters by weaving a reflective strip into the paper, that appears black when copied or scanned.

Another deleterious effect caused by the poor lighting in current scanner technology is that the specular surface of a matte-finish photograph, reflective document or art work will exhibit a myriad of "sparkles" or random point reflections of the off-axis/plane light source off the angled facets within the fine-scale surface undulations. These shortcomings fundamentally limit the ability of linear scanners and copiers to faithfully reproduce many types of documents and art work.

OBJECTIVES OF THE INVENTION

It is an object of the invention to provide a method and apparatus for illuminating an object to be observed by machine vision camera(s) wherein a diffused illumination of the object is produced which is continuous and uniform in nature and is free of dark, bright or void portions capable of generating erroneous vision signals.

Another object of the invention is to provide a method and apparatus for illuminating specular objects to be observed by electronic machine vision cameras, film cameras, scanners, photocopiers or human observers, wherein the object is uniformly illuminated by a primary, off-observation axis source of diffused light emitting from an envelope substantially surrounding the object, having an observation window or viewing orifice to permit vision access along an observation axis that is masked against reflection by the object with a secondary diffuse light source supplied along the observation axis/plane.

Another object of the invention to provide a method and apparatus for illuminating an elongate linear portion or narrow strip of an object to be observed by linear scanners wherein a diffused illumination of the linear portion or strip of the object is produced which is continuous and uniform in nature and is free of dark, bright or void portions capable of generating erroneous vision signals.

Another object of the invention is to provide a method and apparatus for illuminating an elongate linear portion of specular objects to be observed by electronic machine vision cameras, film cameras, scanners, photocopiers or human observers, wherein a linear portion of the object is uniformly illuminated by an elongate primary, off-observation plane source of diffused light emitting from an elongate envelope substantially surrounding the linear portion of the object, having an elongate observation window or viewing orifice to permit vision access along an observation plane that is masked against reflection by the object with a secondary on-observation plane.

Another object of the invention is to provide a method and apparatus for illuminating specular objects to be observed by electronic machine vision cameras wherein the object is illuminated by a diffused light emitting from an off-observation plane diffuse light source of a shape and size sufficient to provide substantially uniform illumination of the object to be observed and an on-observation plane diffuse light source projected through an elongate observation window in the off-observation plane diffuse light source to permit machine vision along an observation plane while masking the observation window against possible reflection from the observed object surface.

Yet another object of the invention is to provide a method and apparatus for illuminating machine vision observed specular objects with an uniform diffused light wherein the observation window is masked against possible reflection from the observed object surface by the introduction of a diffused light through the window along the observation axis/plane of an intensity and character substantially equal to the intensity and character of the primary diffused light illuminating the object.

An additional object of the invention is to provide a method and apparatus for masking vision observation windows against possible reflection in the surface of observed articles by projecting a light through the window substantially identical in character to the primary light illuminating the object.

Still another object of the invention is to provide a method and apparatus for illuminating a machine vision illuminated object having a light reflecting surface wherein a beam splitter is employed to project a diffused light through a camera observation window along the camera observation axis/plane of an intensity and character corresponding to the primary diffused light illuminating the observed object.

Yet a further object of the invention is to minimize the depth of the on-observation axis/plane light source assembly by utilizing a either flat or a curved beam splitter.

SUMMARY OF THE INVENTION

The practice of the concepts of the invention are primarily utilized in machine vision applications with objects having specular surfaces, including surfaces of convex configurations and surfaces containing numerous convex and concave texture elements such as those found in materials such as embossed metal foil, matte-finish photographs and the like. However, it will be appreciated that the inventive concepts disclosed herein are also applicable to film camera, digital camera and microscope-aided human inspection systems, as well to line-scanning image sensors and photocopiers.

The object to be machine vision observed, such as the solder of a printed circuit, a ball bearing, or the like, is illuminated from a given side and given direction by a primary off-observation axis light diffusing source. One form that this primary off-observation axis light diffusing source may take is the form of a translucent dome superimposed over the object which is formed of a translucent material and is backlighted by lamps, or the dome may include an inner light diffusing surface or layer, and an outer light reflecting layer whereby light interiorly projected into the dome is diffused and uniformly illuminates the object over which the dome is superimposed. Another form that the primary off-observation axis light diffusing source may take is the form of a ring-shaped diffuse light source. In fact, the primary off-observation axis light diffusing source may take the form of any suitable shape and size to correspond to the shape and size of any given object to be observed so that the entire object to be observed, or any specific region of said object is substantially uniformly illuminated.

In either embodiment, an observation window or windows, which may be in the form of one or more camera openings or orifices, or other zones of material that appears transparent to a machine vision camera, must be defined in the primary diffuse light source whereby the camera, or other machine vision device, which is located outside the confines of the primary diffuse light source, may have vision access to the object that is located within the primary light source. The line of sight from the camera through the observation window to the object constitutes an observation axis. To prevent the observation window or windows, and the cameras, from reflecting from the surface of the object being observed, and hence creating a false or erroneous signal indicating a fault, a diffused light projector utilizing a flat or curved beam splitter is associated with each observation window to project a secondary, on-observation axis diffused light through the observation window and upon the observed object that is of an intensity and character substantially equal to the diffused light being cast upon the object by the primary diffuse light source, and in this manner the observation window(s), and camera(s) associated therewith, are masked against reflection in the surface of the object being observed by the camera or cameras. Accordingly, by masking the observation window, false signals or reflections from the observed object are prevented and a true camera signal is received capable of accurately interpreting the condition of the observed object free of erroneous signals due to reflections of the lighting or observing apparatus.

Preferably, the diffused light projector is in the form of a beam splitter including a partially silvered mirror or a half silvered membrane pellicle of nitrocellulose or plastic film such as "MYLAR", which has advantageous beam splitting characteristics in certain applications, a light generator, and a light diffusing panel wherein diffused light passing through the diffusing panel is reflected by the partially silvered mirror membrane through the observation window along the observation axis/plane. As the mirror is light pervious, the camera continues to observe the object through the beam splitter mirror and accurately records the surface conditions of the observed object.

In the practice of the invention, a beam splitter similar to those shown in my co-pending application Ser. No. 07/750, 257 filed Aug. 27, 1991, now U.S. Pat. No. 5,187,611 may be employed. The primary light generator and the beam splitter light generator may take several forms as shown in the aforementioned patent, such as incandescent bulbs, fluorescent light bulbs, LEDs, diodes, fiber optics, or the like, and in the practice of the invention control means permit accurate control and variation of the diffused light being generated and reflected by the beam splitter in order to equate the beam splitter projected light to that supplied by the primary diffused light source.

Many machine imaging devices, such as web inspection machines, line-scanning image sensors, and photocopiers, for example, only image an elongate linear portion or narrow strip of the object being imaged, that extends across the width of the object being imaged. In order to image the entire surface of the object being viewed, such devices scan the length of the object by moving the object being scanned relative to the camera and light source.

According to the present invention a linear portion of an object to be imaged is illuminated by an elongate primary off-observation plane light diffusing source. At least one machine vision camera, or other suitable machine vision device, views the illuminated linear portion of the object along an observation plane that extends through a corresponding elongate observation window. To prevent the observation window and the camera from reflecting from the surface of the object being observed, and hence creating a false or erroneous signal indicating a fault, an elongate linear diffused light projector utilizing an elongate flat or curved beam splitter is associated with each observation window to project a secondary, on-observation plane diffused light through the observation window and upon the observed linear portion of the object that is of an intensity and character substantially equal to the diffused light being cast upon the linear portion of the object by the primary diffuse light source. Accordingly, by masking the observation window, the detection of false signals or reflections from the observed object by the machine vision device is prevented.

As will be appreciated from the following description, the apparatus permitting the practice of the invention is relatively simple and inexpensive as compared with prior art devices incapable of providing a true continuous diffused light as provided by the invention.

BRIEF DESCRIPTION OF THE DRAWINGS

The aforementioned objects and advantages of the invention will be appreciated from the following description and accompanying drawings wherein:

FIG. 14 is a diametrical elevational sectional view of another embodiment of a dome envelope having an inner light diffusing surface wherein a ring is mounted at the lower end of the dome and a plurality of lamps are mounted on the ring, the ring including a reflecting surface for reflecting light upwardly into the envelope upon the inner dome diffuse reflecting surface;

FIG. 15 is a plan view of the embodiment of FIG. 4 as taken from the top of FIG. 4 shown in section;

FIG. 16 is a plan sectional view taken along Section 16—16 of FIG. 14;

DESCRIPTION OF THE PREFERRED EMBODIMENT

FIGS. 1–6 depict various illumination geometries that have been traditionally used in machine vision systems along with their associated incident angle brightness histograms. For example, in FIG. 1, a co-axial illumination system 1 is employed to illuminate object 2 as it is viewed by electronic machine vision camera 3. As can be seen from the incident angle brightness histogram shown in FIG. 2, this co-axial illumination system provides a diffuse illumination zone 4 with a desirable incident illumination level that coincides with a zero angle of incidence off of the observation axis but is substantially devoid of any illumination as the angle of incidence deviates from zero.

Figure 3:
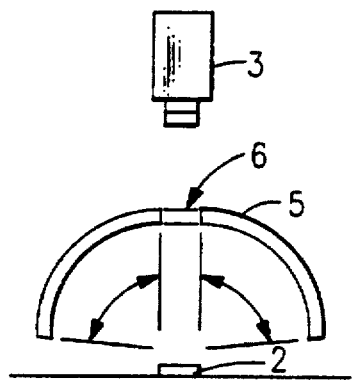
Figure 4:
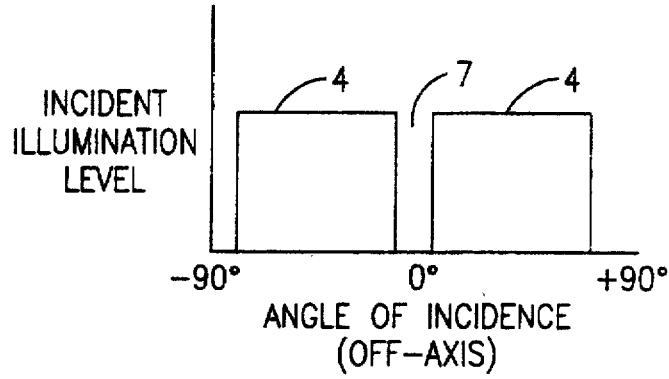

FIG. 3 depicts an off-illumination-axis diffuse dome lighting system 5 illuminating an object 2 to be observed by electronic machine vision camera 3 through an observation window 6, which can be an opening or orifice or even a zone of material that appears transparent to a machine vision camera, such as clear plastic or the like. This illumination system creates the uniform diffuse illumination zone 4 shown in FIG. 4. While the incident illumination level is substantially uniform as the angle of incidence of the light increases away from a zero angle of incidence off of the observation axis, the on-observation axis region 7, which has an angle of incidence approaching zero degrees off-axis, is substantially devoid of any illumination.

Figure 5:
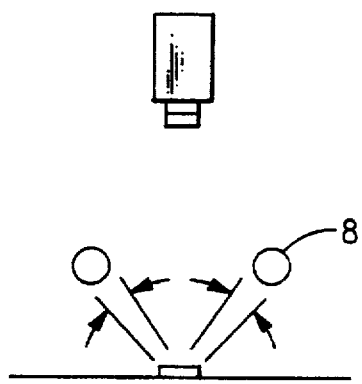
Figure 6:
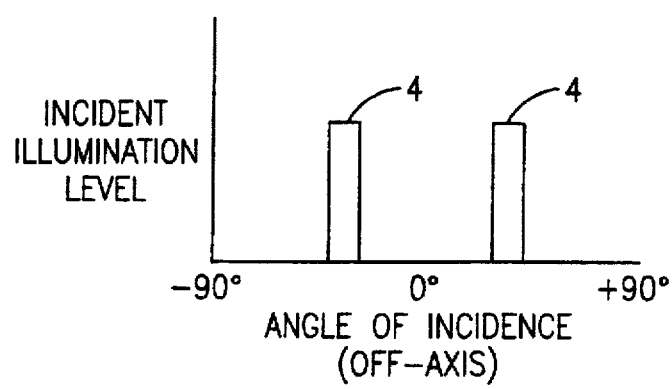
Figure 8:
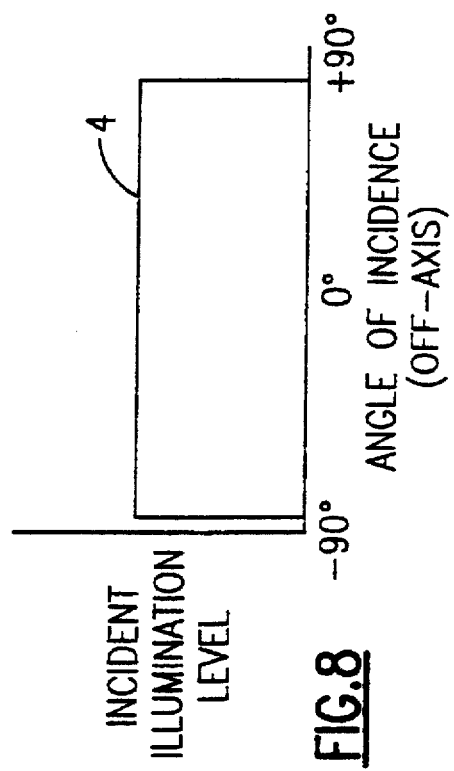
FIGS. 8 and 10 depict the Incident Angle Brightness Histograms associated with the lighting geometries depicted in FIGS. 7 and 9 respectively.

The ring illumination system and its corresponding incident angle brightness histogram, as depicted in FIGS. 5 and 6 respectively, provides a uniform diffuse illumination zone 4 with a substantially uniform incident illumination level that corresponds to substantially the same shape as the ring illuminator 8 being employed.

Figure 7:
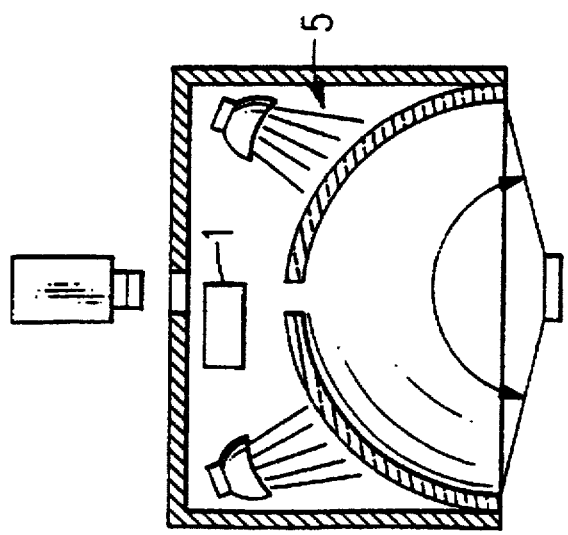
FIGS. 7 and 9 depict two embodiments of Continuous Diffuse Illumination geometries contemplated by the Applicants invention.
Figure 10:
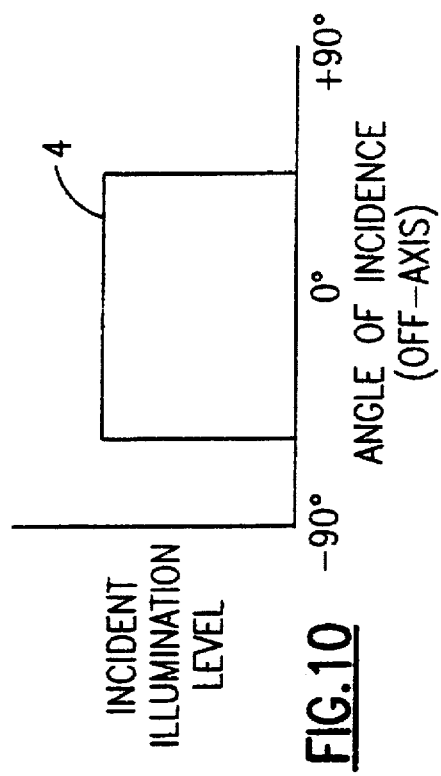

FIGS. 7, 8, 9, and 10 show four embodiments of illumination systems and methods contemplated by the present invention and their respective incident angle brightness histograms. First, FIG. 7 shows a dome-shaped continuous diffuse illumination system that is comprised of a combination of the co-axial illumination system 1 of FIG. 1 and the off-illumination-axis diffuse dome lighting system 5 of FIG. 3. The combination of these two illumination systems results in a lighting environment with the incident angle brightness histogram shown in FIG. 8. This environment is characterized by a diffuse illumination zone 4 with a substantially uniform incident illumination level irrespective of the angle of incidence.

Figure 1:
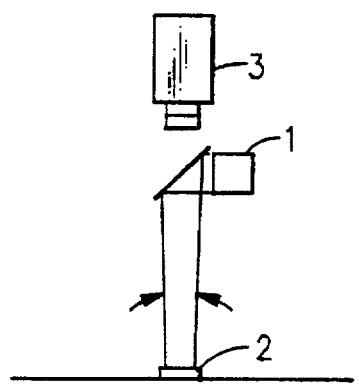
FIGS. 1, 3 and 5 depict traditional illumination geometries used in conjunction with machine vision systems, namely Co-Axial Illumination, Off-Axis Diffuse Dome Illumination, and Ring Illumination respectively.
Figure 2:
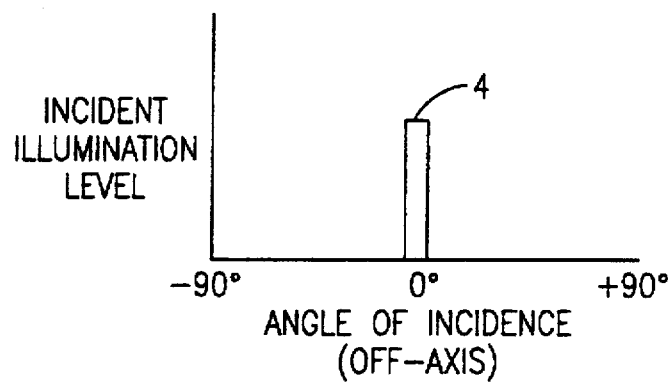
FIGS. 2, 4 and 6 depict Incident Angle Brightness Histograms, which are graphs plotting incident illumination level as a function of angle of incidence, associated with the lighting geometries depicted in FIGS. 1, 3 and 5 respectively.
Figure 9:
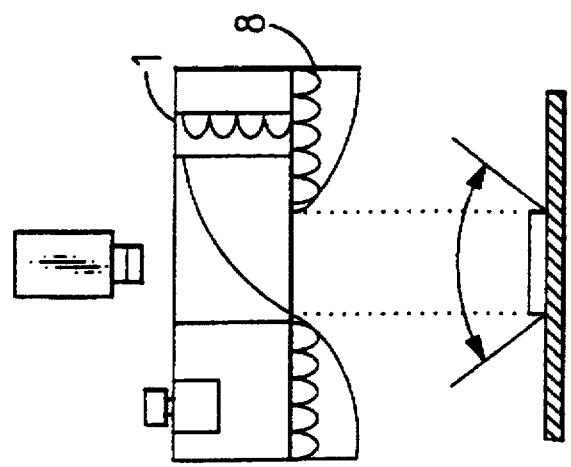

FIG. 9 depicts another embodiment of the invention wherein the co-axial illumination system 1 of FIG. 1 is combined with the ring illumination of system 8 of FIG. 5 in order to create a continuous diffuse ring illumination system. The lighting environment created by this system is shown by the incident angle brightness histogram shown in FIG. 10, wherein a substantially uniform incident illumination level is produced over a specific region whose shape and size is dependent upon the shape and size of the ring illumination system.

Figure 11:
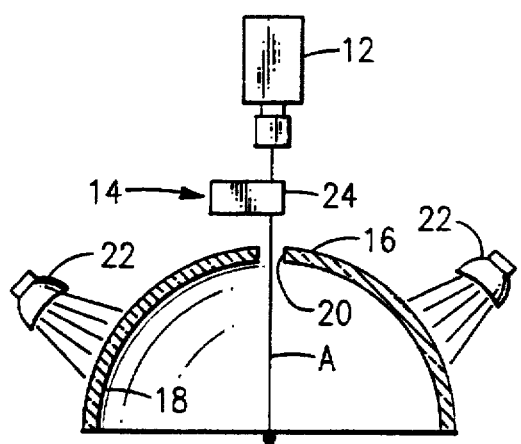
FIG. 11 is a schematic elevation view of the basic apparatus and relationships thereof permitting the practice of the invention with a back lighted translucent dome diffused light primary source.

A simplified schematic arrangement of components illustrating one embodiment of the inventive concepts is shown in FIG. 11, wherein the object to be viewed by a machine vision television camera is indicated at 10. The object 10, which normally, in the practice of the invention, would include a shiny or specular surface, such as the soldered surfaces of a printed circuit board, or a spherical ball bearing, reflective packaging surface, or the like, and often is of an irregular or non-flat configuration, is viewed by a camera indicated at 12. The viewing of the object 10 by the camera 12 occurs along the observation axis A as indicated in FIG. 11. Usually, the purpose of viewing the object 10 by the camera 12 is for the purpose of inspecting the object 10 for flaws; however, the observation may be for any desired reason, such as for purposes of machining orientation or assembly prior to subsequent machining operations, or reading or reproducing printed, inscribed or chemical or laser etched art work or print. The concepts of the invention are particularly suitable for flaw detection in that a truly uniform lighting of the object 10 is achieved wherein significant variations in light reflected from the object will result only from localized surface slopes greater than half the incident illumination angle, such as are commonly associated with surface imperfections, and not undesired reflections from normal deviations in surface geometry that are not associated with defect conditions.

In accord with the concepts of the invention, a light projector 14 is incorporated between the object 10 and the camera 12 within the observation axis A, and a substantially uniform primary illumination of the object 10 is achieved by a translucent back light hemispherical dome or envelope 16 located over the object 10 as will be appreciated from FIG. 11. The translucent dome 16 may be formed of clouded or treated glass, or may be synthetic plastic or the like whereby light passing therethrough is uniformly diffused. The dome includes an inner surface 18 disposed toward the object 10 and an observation window or opening 20 is formed in the dome 16 to accommodate the observation axis A. The dome 16 is illuminated from the rear by a plurality of lamps 22 casting light upon the outer surface of the dome 16 and this light is diffused and emits from the inner surface 18 upon the object 10 to uniformly illuminate the object 10 for observation by the camera 12.

If the object 10 includes a shiny, specular surface, as occurs when viewing solder, ball bearings, reflective packaging, and the like, the surface of such an object will reflect the image of the dome observation window or opening 20, through which the camera viewing occurs, along axis A. As no light is emitting from the window 20 with a conventional illuminating dome, the window 20 will appear as a dark or dead spot in the dome 16 which will be observed by the camera 12, and the camera will sense the dark reflection of the window 20 as a defect, unless the camera output is programmed to ignore this window reflection. If the camera program ignores the window reflection, an imperfection on the object 10 coinciding with the observation axis A will not be sensed by the camera 12 permitting a flawed object to pass inspection.

To overcome the aforementioned problems resulting from the reflection of the window 20, the light projector 14 projects secondary diffused light through the window 20 upon the object 10 along the observation axis A. In this manner, the window 20 no longer appears as a dark spot upon the inner surface 18 of the dome 16, and as the projected light emitting from the beam splitter 14 is of an intensity and character substantially equal to the primary diffused light passing through the dome 16 as generated by the lamps 22, the dome 16 is free of dark or dead spots and a true uniform illumination of the object 10 is achieved and defects on the object 10 coinciding with the observations axis A will be detected by the camera 12.

In the preferred embodiments, the light projector 14 is a beam splitter and includes a housing 24 in which a mirror 26 is located. The mirror 26 may be disposed at an angle with respect to the observation axis A, and the mirror includes a face 28 disposed toward the camera 12 and a face 30 disposed toward the object 10.

The surfaces 28 and/or 30 the mirror 26 are conventionally provided with silvered strips, or otherwise treated, wherein the mirror 26 constitutes both a reflective surface and a light pervious surface wherein light may pass through the mirror 26 from the object 10 for observation by the camera 12, and the mirror 26 also reflects the diffused light generated by the beam splitter light source, as later described. Alternatively, the beam splitter mirror 26 can be formed by a half silvered membrane pellicle of nitrocellulose or plastic material, such as "MYLAR", which has advantageous beam splitting characteristics in certain applications.

Figure 12:
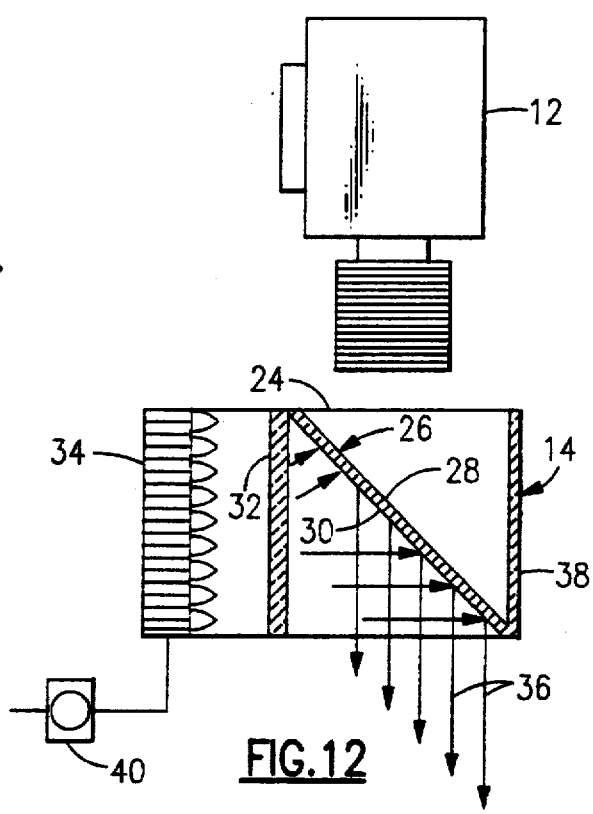
FIG. 12 is an enlarged detail view of the beam splitter and television camera used in the practice of the invention, the beam splitter being shown in section.
Figure 12A:
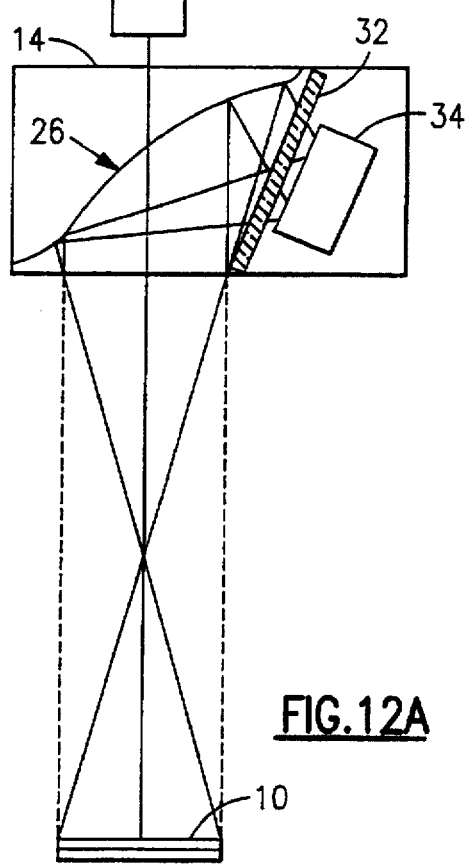
FIG. 12A is an enlarged detail of a curved beam splitter used in the practice of the invention, the beam splitter being shown in section.

Either of the above materials used as the beam splitter mirror 26 may be provided in a curved configuration having a concave face disposed towards both the object 10 and the secondary light source 34 and a convex face disposed towards the observation means, which may be a machine vision camera, as shown in FIG. 12A. This configuration provides an increased range of incident angles for the on-observation axis diffused light source while at the same time reducing the required height of the light projector 14 above the object being viewed.

The light projector 14 includes at least one translucent light diffusion panel 32 formed of treated glass, plastic, or other light translucent material capable of evenly diffusing light cast upon the panel 32 by the secondary light source 34. The secondary light source 34 may consist of a plurality of lamps, diodes, LEDs or optical fibers, or a single fluorescent lamp capable of generating a relatively uniform panel of light cast upon the diffuser 32. Diffused light passing through the diffuser 32 illuminates the mirror 26 and is projected in the direction 36 indicated by the arrows. It will be appreciated that the light direction 36 is coaxial with and coincides with the observation axis A.

The size of the mirror 26 is such that the secondary diffused light reflected therefrom along arrows 36 is sufficient to completely occupy the observation window 20, such that the window 20 will be "filled" with the secondary diffused light emitting from diffuser panel 32 and secondary light source 34. It will be understood that the light projector 14, secondary light source 34 and translucent light diffusion panel 32 may be adjusted in size, shape and relative proximity to create continuous uniform illumination across object of different sizes or at different working distances. For example, an elongate linear strip extending across the object may be illuminated with an elongate illuminator according to the invention, as described later.

The light projector 14 includes a light absorbing panel 38, and the intensity of the light generated by the secondary light source 34 is adjustable by the light control rheostat 40 to ensure that the intensity of the character of the secondary light 36 will be substantially equal to the primary light diffused by the dome 16 and cast upon the object 10 by the lamps 22 and thereby provide a truly continuous diffuse light source.

The light projector 14 is similar in many respects to that shown in my U.S. Pat. No. 5,187,611, the contents of which are incorporated herein as of reference, and the beam splitter concepts shown in this patent are applicable in the instant application.

By regulating the light control 40, the secondary diffused light 36 projected through the window 20 will equal in intensity and character the primary diffused light being cast upon the object 10, and the use of the inventive concepts completely eliminates false readings which would otherwise be picked up by the camera 12 due to the reflection of the window 20, and the camera there behind, as reflected by the surface of the object 10. In the practice of the invention, the window 20 is neutralized and a truly continuous diffused light source of the object 10 is achieved eliminating false readings by the camera 12 and permitting a true 100% inspection of that side of the object 10 observable by the camera 12.

Figure 13:
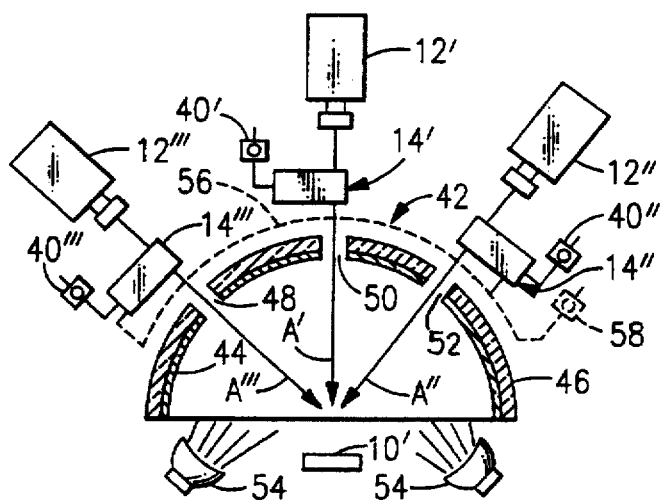
FIG. 13 is a schematic illustration of apparatus practicing the principles of the invention wherein the diffused light illumination dome employs an inner light diffusing surface and an outer light reflecting surface, and a plurality of cameras and observation orifices are employed, the dome being shown in section.

A variation of the inventive concepts is shown in FIG. 13. In FIG. 13, three dome observations windows, cameras and light projectors permit viewing of the object from various angles, and the diffused light source dome is interiorly lighted to produce a more concise assembly of components than that possible with the exteriorly lighted arrangement shown in FIG. 11.

In the embodiment of FIG. 13, components similar to those previously described are indicated by primes, and these components function in a manner identical to that described above.

In FIG. 13, the illuminating dome 42 is located above the object 10' to be observed, and the dome 42 includes an inner hemispherical layer 44 of diffuse reflective paint. The construction is such that light cast upon the layer 44 interior of the dome 42 is diffusely reflected inwardly upon the object 10', providing a primary illumination effect similar to that achieved with the embodiment of FIG. 11.

The dome 42 is provided with three observation windows as indicated at 48, 50 and 52, and opening 50 is associated with a camera 12' and light projector 14', while opening 52 provides an observation window for camera 12" and light projector 14", while window 48 provides access for the observation axis A''' of the television camera 2''' as associated with the light projector 14'''.

The primary light source for the dome 42 is provided by the lamps 54 located adjacent the object 10' and directed toward the interior of the dome 42 such that the reflective layer 44 receives the light emitting from the lamps 54 and the light reflected from the layer 44 is diffused by layer 44 for illuminating the object 10' with a uniform diffused light. By locating the lamps 54 adjacent the object 10' the overall dimensions and relationship of components is more concise than the illustrated embodiment of FIG. 11, and size and configuration advantages exist with the embodiment of FIG. 13.

The light projectors 14', 14", and 14''' of the embodiment of FIG. 13 may utilize separate lamp controlling rheostats 40', 40" and 40''', respectively, whereby the various light projectors are separately controllable so that any minute light variations that may occur at the window 48, 50 and 52 may be accommodated. However, it is also possible to connect the light sources of the three light projectors in parallel by a circuit 56, as represented in dotted lines in FIG. 13, controlled by a single rheostat 58.

The concepts of the operation of the embodiment of FIG. 13 are identical to those described above with respect to FIG. 11. The observation axis of each of the three cameras is directed toward the object or objects of interest 10', and the dome observation window through which each camera observation axis extends is filled with diffused light projected from the associated light projector so as to eliminate any false readings which would otherwise exist due to the reflection from the surface of the object 10' of the windows 48–52.

With conventional illumination domes, the existence of a plurality of cameras to permit viewing of the object from various angles also resulted in a plurality of reflected dark spots due to the presence of the observation windows in the dome increasing the likelihood of false readings, and the possibility of overlooking flaws in the observed object.

In the practice of the invention regardless of the number of windows formed in the dome a continuous, uniform light source for the observed object is provided and any shadows or dark reflections from the object 10' will represent flaws, and not reflections from non-uniformities in the illuminating dome structure itself.

In FIGS. 14–16, another embodiment for illuminating an object with diffused light utilizing the concepts of the invention is illustrated. In this embodiment, an envelope or dome generally indicated at 60 is formed of either an opaque material or a translucent material having a lower bell configuration having an outer surface or layer 61 and an inner surface or layer 63. The layer 61 is internally silvered, or the like, to function as a mirror or efficient reflector of light, and the inner surface 63 constitutes a light diffusing layer whereby light within the dome 60 will be reflected by the layer 61 and diffused by the layer 63.

The dome 60 includes a lower annular edge 62, and an upper region that includes a cylindrical neck 64 open at opening 66. An annular aperture 68 is defined within the dome 60 at the upper region of the bell portion, and an electronic camera, such as a television camera, not shown, is adapted to be located above the dome 60 having an observation axis coaxial with the axis of the dome 60 as presented by dotted lines 70. The observation axis as represented by lines 70 is in alignment with the light reflecting object to be illuminated and viewed as shown at 72.

A beam splitting partially silvered mirror 74 is mounted within the neck 64 disposed at an angle to the observation axis. The mirror 74 may be embedded into the neck 64 as at 76, or otherwise attached to the neck, a plurality of lamps 78, which may constitute diodes, incandescent or fluorescent lamps, LEDs or the like, are mounted exteriorly of the neck 64 upon a bracket 88, attached to the neck 64 by pins 84, FIG. 5.

The dome neck 64 is translucent and constitutes a light diffuser whereby the light entering the neck 64 emitting from lamps 78 is diffused prior to being reflected from the mirror 74. Light passing through the partially silvered beam splitter 74 passes through the opening 80 formed in neck 64 which is in opposed relationship to the lamps 78. A light absorbing panel 86 is mounted upon the bracket 82 for absorbing light emitting from lamps 78 and passing through the mirror 74. Bracket 82 is attached to neck 64 by the pins 84. Of course, it will be appreciated that the light reflecting surface 61 defined on the bell portion of the dome 60 does not extend to the exterior surface of the neck 64, as it is necessary that light emitting from lamps 78 enter the neck 64 and a portion of such light is reflected from the mirror 74 downwardly along lines 70 upon the viewed object 72.

An annual ring 90 is attached to the lower end of the dome 60 adjacent the lower edge 62 by a plurality of fasteners 92. The cross sectional configuration of the ring 90 will be appreciated from FIG. 14, and the ring includes an inwardly radially projecting lip upon which an annular reflecting surface 94 is formed. The reflecting surface 94 may be silvered to increase its light reflecting capabilities, and the surface 94 is obliquely related to the horizontal whereby light impinging on the surface 94 will be reflected internally into the bell portion of the dome 60. The ring 90 may also be made of translucent material machined to a thickness causing the light diffusely transmitted through the ring to be equal in intensity to the light reflected off of the inside of the bell portion of the dome.

A plurality of lamps 96 are mounted within the ring 90 evenly spaced about the circumference of the ring as will be appreciated from FIG. 6. The lamps 96 directly illuminate the reflecting surface 94 and the lamp light is efficiently reflected into the dome 60 for passing through the diffusing layer 63, reflecting from the reflecting layer 61 and impinging upon the object 72 wherein the object 72 is prevented from being directly illuminated by the lamps 96. Accordingly, all of the light illuminating object 72 will be diffused light as reflected by surface 61 and diffused by layer 63.

Rheostats, or other lamp control means, not shown, may be used to control the intensity and character of the light emitting from lamps 78, as described with respect to the above embodiments.

The apparatus of FIGS. 14-16 functions in a manner similar to that described above with respect to the embodiments of FIGS. 11 and 13. The lamps 78 are illuminated whereby secondary diffused light will be reflected from beam splitter mirror 74 upon object 72. The electronic television camera, not shown, produces an observation axis as represented by dotted lines 70 for viewing the object 72.

Primary illumination of the object 72 results from the lamps 96 whose light is reflected into the bell portion of the dome 60 and the resultant diffused light illuminates object 72. By controlling the intensity of the lamps 78, the secondary light entering the bell portion of the dome 60 through the aperture 68 as reflected by the mirror 74 can be adjusted such that the reflected secondary diffused light is substantially equal in intensity and character to the primary diffused light reflected by layer 61 as diffused by layer 63. In this manner, the illumination apparatus of FIGS. 14-16, also, illuminates any "dark spot" at the aperture 68 preventing a dark reflection from the light reflecting object 72 which would be sensed by the camera and produce an erroneous and misleading signal as to the character of the surface of the object 72. The embodiment of FIGS. 14-16 is concise, rugged, and readily lends itself to many applications.

Of course, the reflector dome 60 could be constructed in a manner different than that disclosed above. For instance, the bell portion of the dome could be formed of turned or spun aluminum having an internal light diffusing reflecting surface and the tubular neck can be formed of a translucent material and mechanically attached to an aluminum bell portion. Further, the beam splitter mirror 74 can be formed by a half silvered membrane pellicle of nitrocellulose or plastic film, such as "MYLAR", which has advantageous beams splitting characteristics in certain applications.

Figure 17:
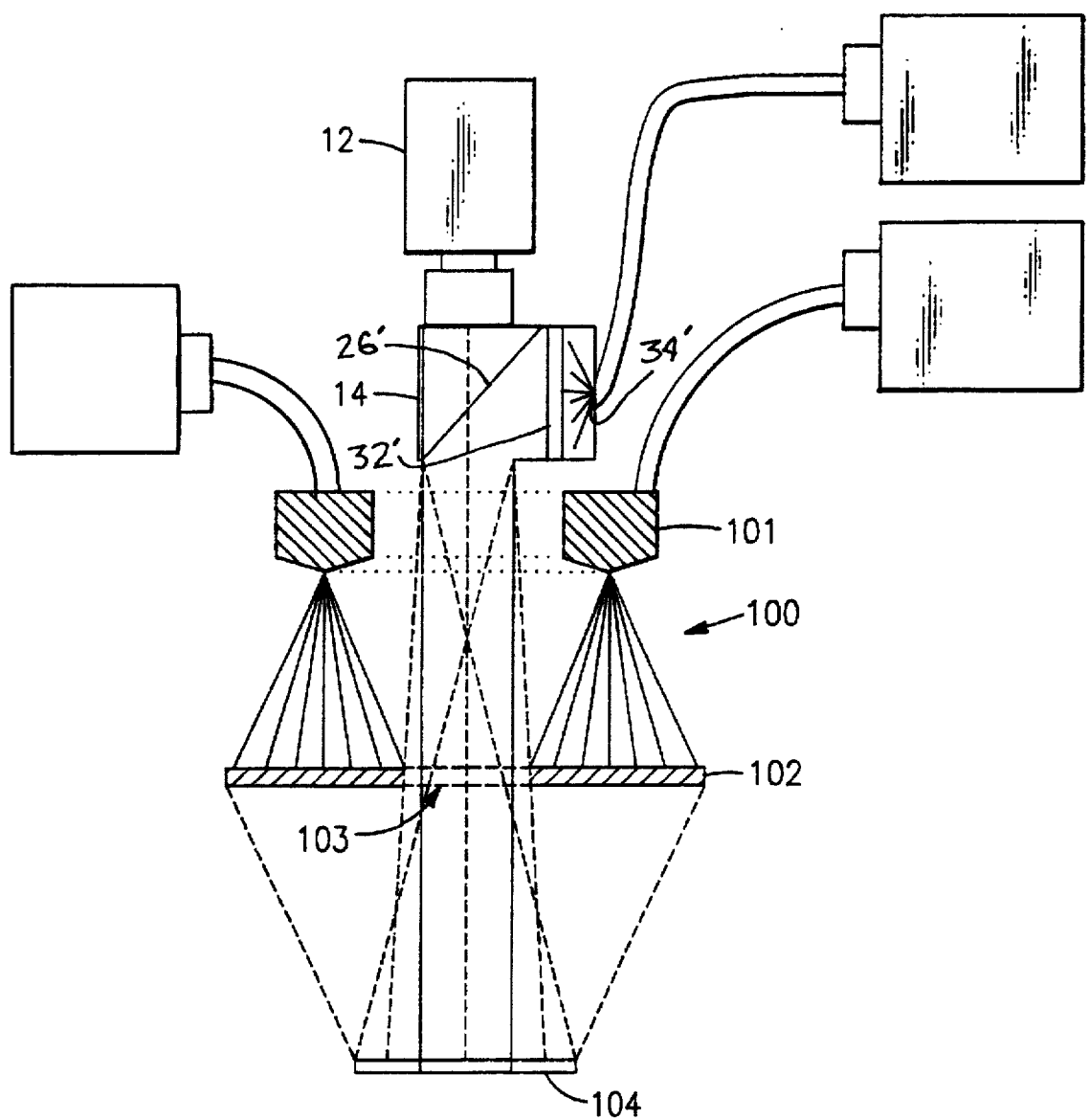
FIG. 17 is a schematic elevational view of another embodiment of the apparatus and relationships thereof permitting the practice of the invention with a back lighted translucent ring-shaped diffused primary light source, shown in section.

A further embodiment of the inventive concept is shown in FIG. 17. In FIG. 17, the camera 12 and light projector 14 operate in like manner as those described earlier for the other embodiments of the inventive concept previously disclosed. However, the primary off-observation axis diffuse light envelope or dome is replaced by a primary off-observation axis ring illuminator 100.

The ring illuminator 100 is comprised of a primary light source 101 and a diffuser tins 102. The primary light source may be a fiber optic ring illuminator, an LED array illuminator, or even a standard fluorescent ring lamp. Similar to the primary diffuse light envelopes or domes described above, the diffuser ring 102 also has an observation window 103 disposed therein to provide vision access, along an observation axis to the area 104 being observed by the camera 12. The light projector 14 effectively "fills the hole" in the primary diffuse light source created by the observation window 103 with diffused light that can be adjusted such that it is substantially equal in intensity and character to that provided by the ring illuminator.

Figure 18:
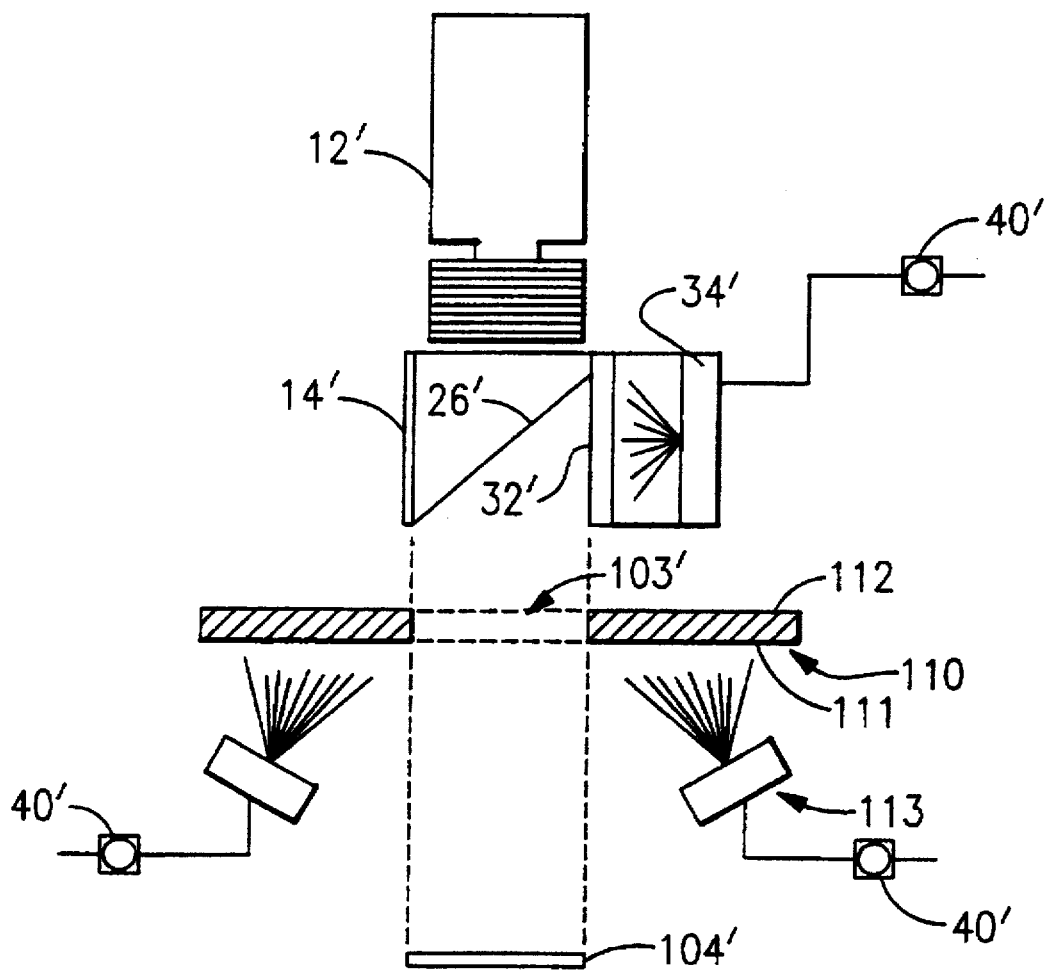
FIG. 18 is a schematic illustration of an apparatus practicing the principles of the invention wherein the diffused ring illuminator employs an outer light reflecting surface, shown in section.

Another variation of the inventive concepts is shown in FIG. 18. In FIG. 18, a diffuse reflector 110 takes the place of the diffuser ring utilized in the embodiment shown in FIG. 17 and the diffuse reflector is interiorly lighted by primary light source 113 to produce a more concise assembly of components that is possible with the arrangement shown in FIG. 17. In the embodiment of FIG. 18, components similar to those previously described are indicated by primes, and these components function in a manner identical to that described above.

In FIG. 18, the diffuse reflector illuminator 110 is located above the area 104' that is to be observed and the diffuse reflector 110 includes an inner layer 111 that is translucent and capable of diffusing light reflected by the diffuse reflector outer layer 112, which may be in the form of a mirror. The construction of the layers 111 and 112 is such that light cast upon the inner layer 110 of the diffuse reflector 110 is reflected from the outer layer 112 through the translucent layer 111 which diffuses the light reflected from outer layer 112 such that the light reflected inwardly upon the area to be observed 104' is uniformly diffused providing a primary illumination effect similar to that achieved with the embodiment of FIG. 17.

The concepts of the operation of the embodiment of FIG. 18 are identical to those described with respect to those previously described. The observation axis of the camera is directed toward an area to be observed 104', and the diffuse reflector observation window through which the camera observation axis extends is filled with diffused light projected from a light projector so as to eliminate any false readings which would otherwise exist due to the reflection from the surface of the area of the observation window 103'.

Figure 19:
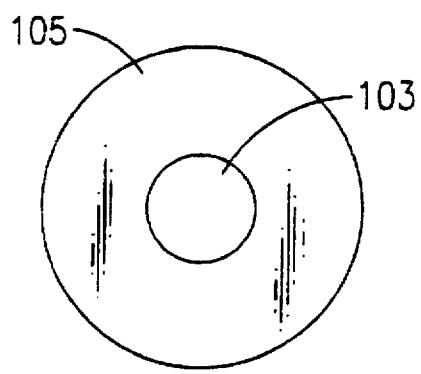
FIG. 19 is an end view of an off-axis ring illuminator geometry particularly suited for viewing circular shaped objects or areas.
Figure 20:
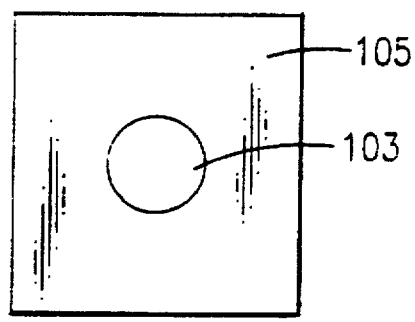
FIG. 20 is an end view of an off-axis ring illuminator geometry particularly suited for imaging square objects or areas.
Figure 21:
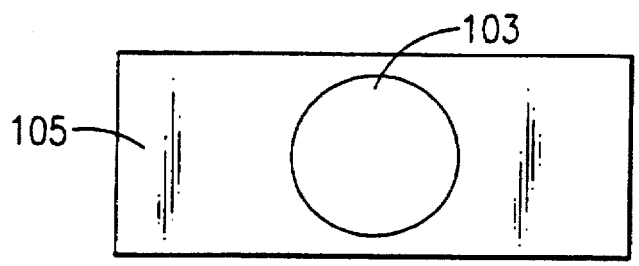
FIG. 21 is an end view of an off-axis ring illuminator geometry particularly suited for imaging rectangular shaped objects or areas.

The illuminator used in either of the embodiments depicted in FIGS. 17 or 18 has a perimeter shape and size that correlates to the viewing geometry, the aperture size of the viewing optics, and the size of the area being observed A variety of illuminator geometries are shown in FIGS. 19-21. For example, the geometry shown in FIG. 19 is particularly suitable for viewing circular shaped areas. The geometry shown in FIG. 20 is suited for viewing square shaped areas and the geometry shown in FIG. 21 is preferable for viewing rectangular shaped areas. Each of these illuminators has an on-observation axis observation window 103 through which a secondary on-observation axis light source is projected and a primary off-observation axis illumination area 105.

Figure 22:
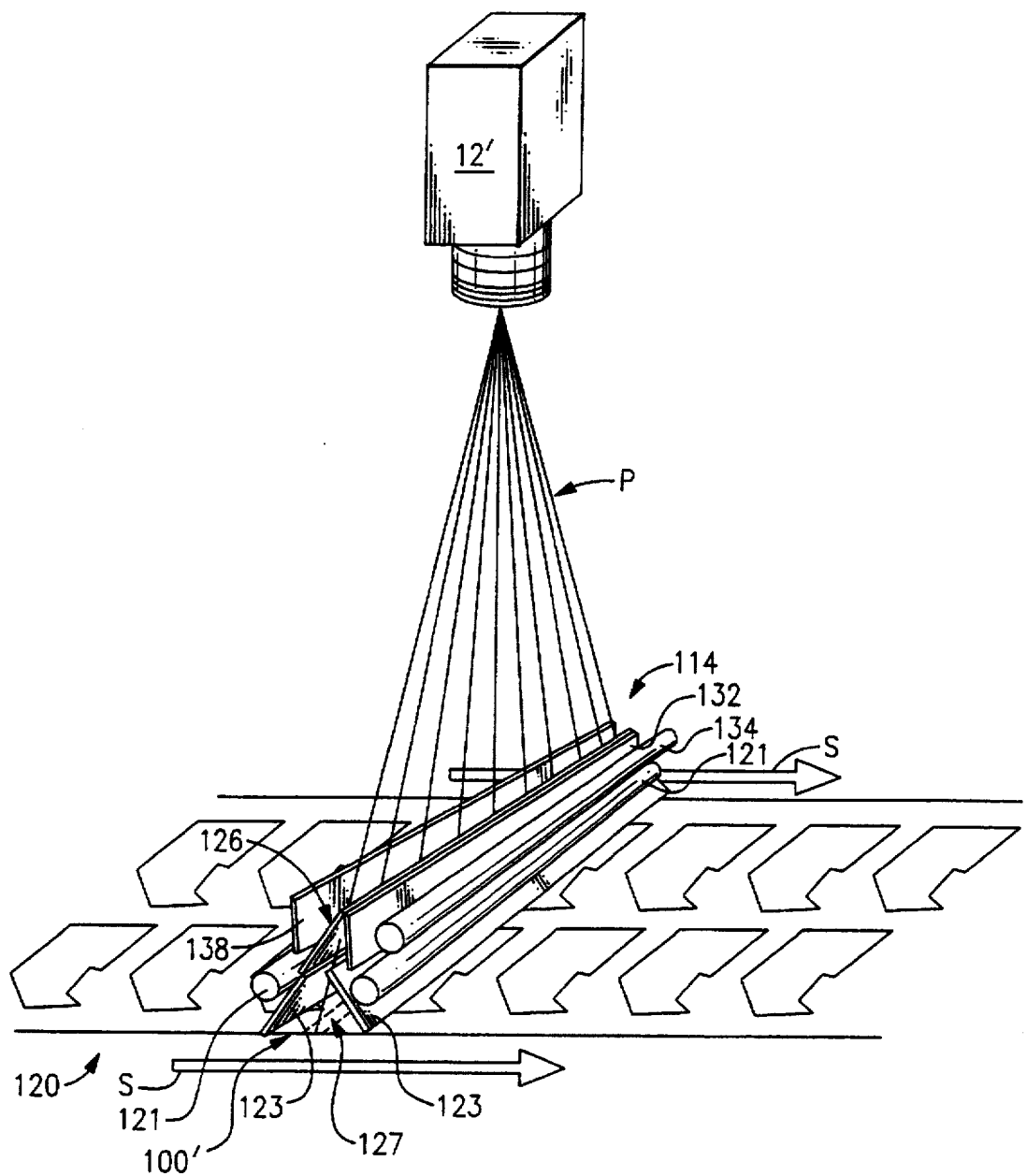
FIG. 22 is a schematic, perspective view of an embodiment of a linear continuous diffuse illuminator according to the invention.

A further embodiment of the inventive concept of the present invention is shown in FIG. 22. In that Figure, the camera 12' and light projector, shown generally as 114, operate in a similar manner as those described in the previously disclosed embodiments. However, the primary off-observation axis diffuse light envelope or dome is replaced by an elongate primary illuminator 100'. The primary linear off-observation plane illuminator 100' is similar to the off-observation axis ring illuminator 100 of FIG. 17 but is elongated in one dimension or direction.

Figure 23:
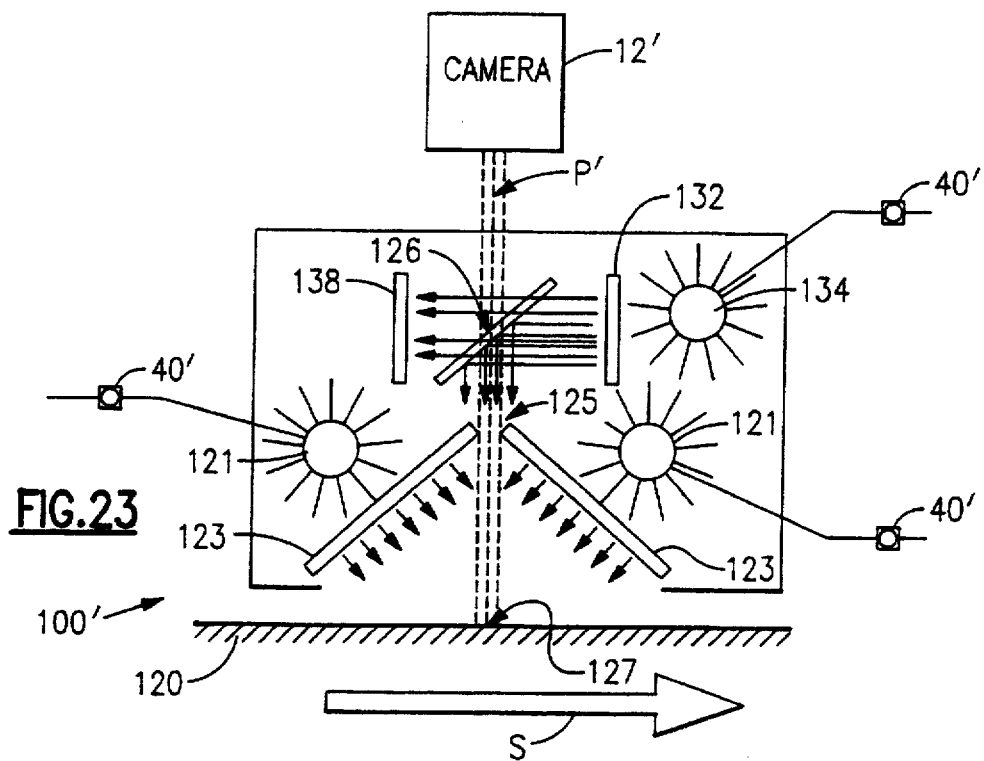
FIG. 23 is a sectional view of the linear continuous diffuse illuminator of FIG. 22.

The elongate primary illuminator 100' comprises a pair of elongate primary light sources 121 and a pair of elongate primary diffusers 123 each disposed at an acute angle relative to the surface of the object 120 being imaged, as best seen in FIG. 23, to provide primary diffuse illumination of a linear portion or strip 127 of the surface of the object 120 being imaged. Similar to the primary diffuse light envelopes or domes described above, the elongate primary illuminator 100' has an observation window 125 formed therein that is elongate to provide vision access along an observation plane of the linear portion 127 of the object being observed by the camera 12'.

An elongate linear light projector 114 effectively "fills" the elongate "hole" in the linear primary diffuse light source created by the observation window 125 with secondary diffused light supplied along the observation plane. The illumination characteristics of the light can be adjusted via rheostat 40' such that the light is substantially equal in intensity and character to that provided by the primary diffuse light source. The elongate light projector 114 comprises an secondary elongate light source 134, an elongate translucent secondary diffuser 132, an elongate beam splitter 126, and an elongate light absorption panel 138. By this arrangement, the observation window is filled with diffused light and masked by the light projector.

The light sources 121, 134 may consist of an elongate array of lamps, diodes, LEDs or optical fibers, or a single elongate florescent lamp capable of generating relatively uniform light which is cast upon the secondary diffuser 132. The intensity of each of the light sources 121, 134 can be controlled using separate rheostats 40' or other suitable control devices. By adjusting the intensity of the light sources 121, 134 until the intensity of the light projected by the light projector through the observation window is substantially the same as the intensity and character of the diffused primary light source, the observation window is completely masked in the same manner as the previously disclosed embodiments.

Each component of the elongate illuminator performs an identical function to the corresponding components of the previously disclosed embodiments. In this embodiment, however, the components are elongate to illuminate uniformly a relatively long and narrow strip of an object being imaged. It can be appreciated that the embodiments of FIGS. 7, 9, 11, 12A, 13, 14, 17 and 18, for example, could be readily modified to be an elongate illuminator, e.g. by elongating the opening, the illumination sources, the diffusers, the beam splitter and the light trap.

The elongate illuminator of FIGS. 22 and 23 is preferably of a length sufficient to span and illuminate the entire width of an object 120 to be imaged, i.e. an elongate strip extending entirely across the object 120 to be viewed, for imaging by the camera 12'. In order to image the entire surface of the object 120 being imaged, i.e. the length and width, the object is moved relative to the elongate illuminator, as indicated by arrow S, such that the illuminator scans the entire length of the object 120.

The linear continuous diffuse illuminator is designed for use with linear scanners, such as line scan cameras and photocopiers, and provides a continuous diffuse illumination environment for a linear area to be imaged. With the basic geometry of the continuous diffuse illuminator disclosed above, the illumination field of a scanner or copier can be made continuous and uniform, allowing accurate reproduction of documents and art work with unseen and/or specular surface finishes as well as those with diffuse surfaces. With such uniform diffuse lighting, smooth and uneven specular surfaces appear uniformly bright. Uneven textured photographic surfaces are made to appear glint-free. The linear continuous diffuse illuminator allows linear scanning devices of all kinds to faithfully reproduce subject matter with both specular and diffuse surface textures by nullifying the effects of uneven surface geometry of specular surfaces.

Figure 24:
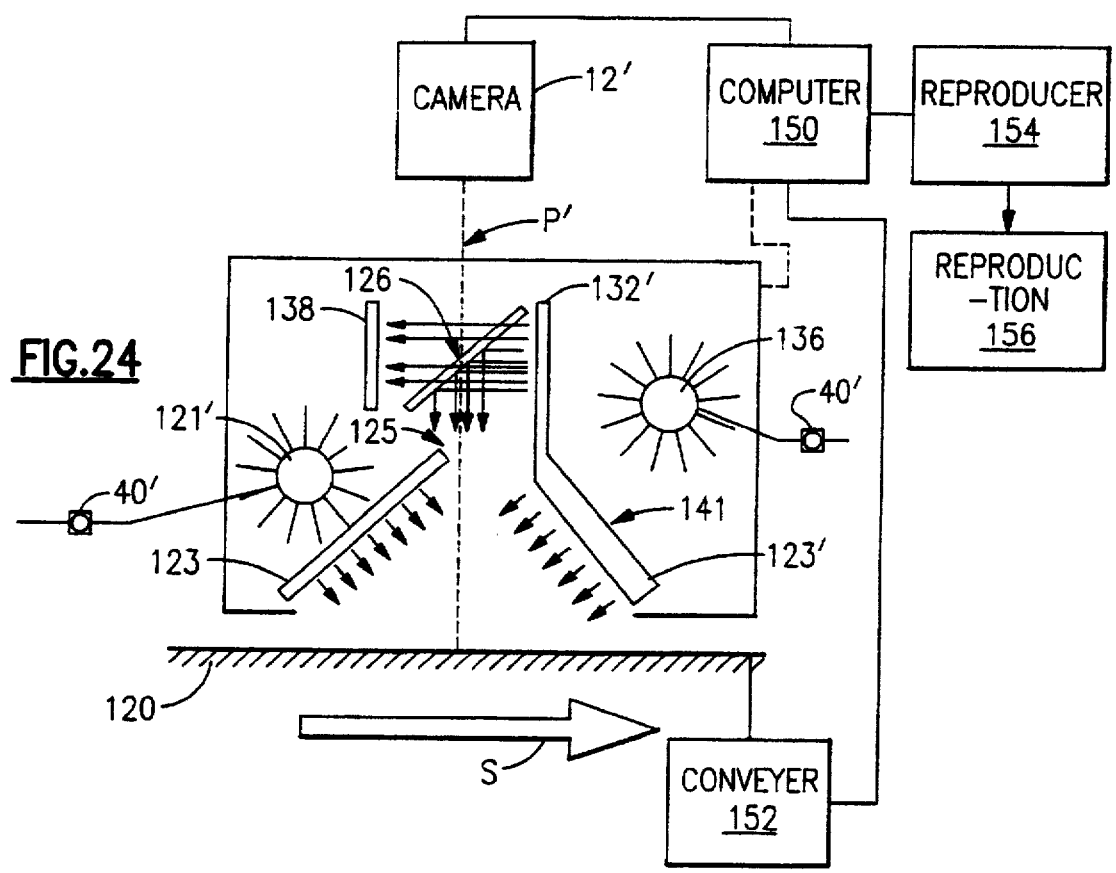
FIG. 24 is a sectional view of another embodiment of a linear continuous diffuse illuminator that has been modified to require only two elongate lamps.

A second embodiment of an elongate illuminator is schematically illustrated in FIG. 24 in diagrammatic cross section. In this embodiment, one of the primary light sources 121 of the previous embodiment has been combined with the light projector light source 134 to form a single light source 136, thereby reducing the number of light sources from three to two.

The number of diffusers is likewise reduced from three to two by combining one of the primary light diffusers 123 with the light projector secondary diffuser 132 to form a single combined diffuser 141. The combined diffuser 141 has two sections, a primary diffuser section 123' and a secondary diffuser section 132'. A portion of the light emitted from the combined light source 136 is diffused by the primary diffuser section 123' and provides direct, primary illumination of a desired area of the object being imaged. Second portion of the light emitted from the combined light source 136 is diffused by the secondary section 132' and is reflected by the beam splitter 126 to illuminate, along the observation plane, an elongate portion of the object being imaged. Reducing the number of light sources and diffusers lowers the power requirement and manufacturing cost of the elongate illuminator and also assists with providing a more compact unit.

The secondary diffuser section 132' is thinner than the primary diffuser section 123'. The relative thinness of the secondary diffuser section 132', in comparison to the primary diffuser section 123', is selected so as to compensate for the partial reflectivity of the beam splitter 126 and provide light reflected by the beam splitter through the observation window of substantially the same intensity as that illuminating the object via the primary diffuser section 123' of the combined diffuser 141. Alternatively, the intensity of the light may be balanced by forming the primary diffuser section 123' more opaque than the secondary diffuser section 132'. Lastly, adjustment of the rheostat 40' can also facilitate such balancing as well.

In this embodiment, the illumination device may communicate, via suitable wiring or cabling, with a computer 150, containing a central processing unit, a RAM, a ROM and a memory, which can control operation of the illumination device, e.g. control the rheostats 40', control the focus of a lens incorporated therein, etc. The camera 12', used in combination with the illumination device, generates and supplies an input of the sensed image to the computer 150 via suitable wiring or cabling. The computer 150 is also connected, via suitable wiring or cabling, to a scanning or conveying apparatus or means 152 which conveys the object to be observed relative to the illumination device and the camera 12', as can be seen FIG. 24. It is to be appreciated that, if desired, the illumination device and the camera 12' can be moved relative to the object by the scanning or conveying apparatus or means 152. The computer 150 then transmits, via suitable wiring or cabling, the sensed image to a reproducing device 154, such as a printer, a thermal imaging device or the like where a reproduction of the observed or sensed image is outputted as a reproduction 156. Alternatively, the sensed image may be send to some other device where the sensed image is further processed in some manner, e.g. the sensed image is compared to a test image.

Figure 25:
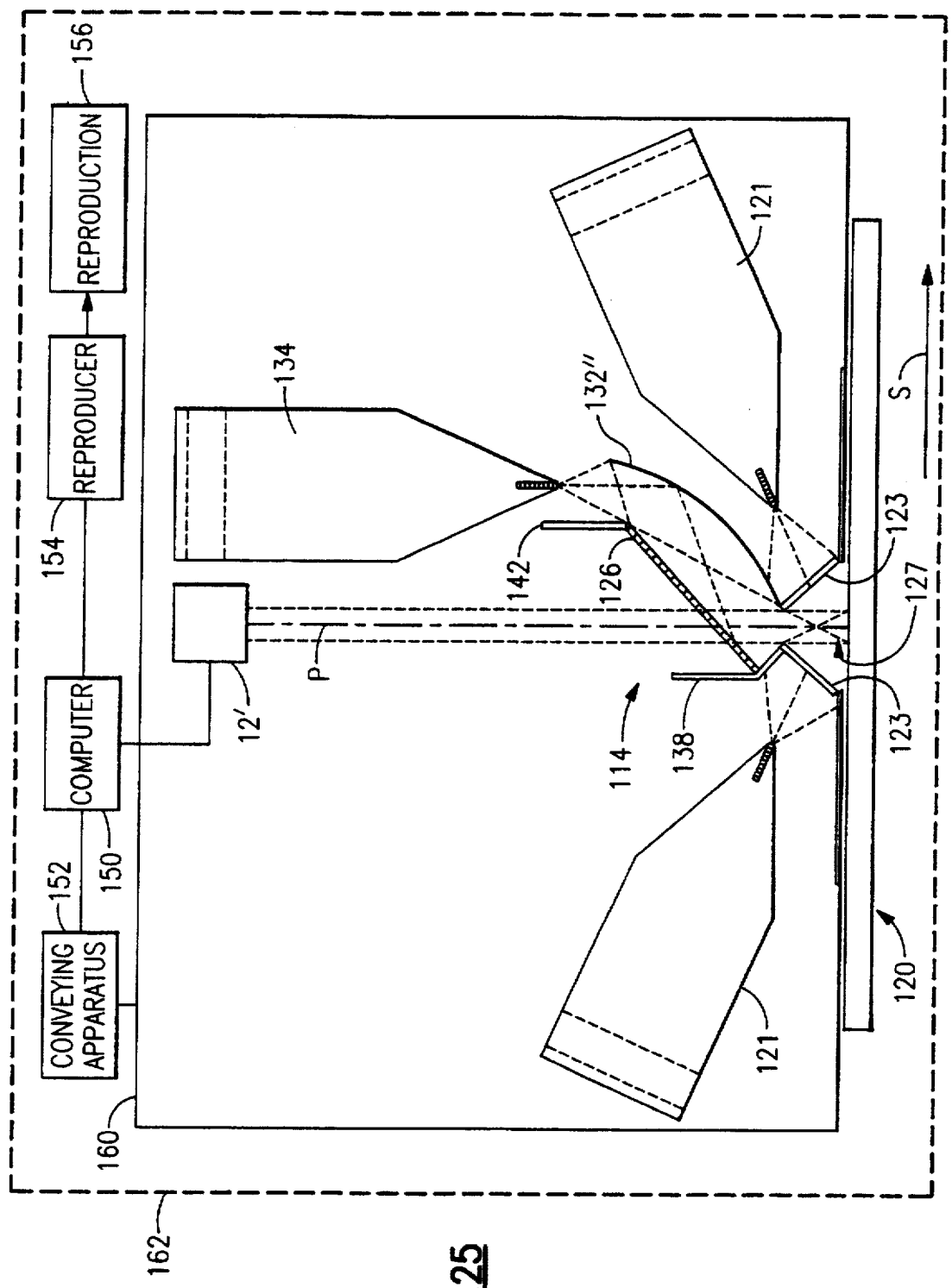
FIG. 25 is a sectional view of another embodiment of a linear continuous diffuse illuminator that has a curved secondary light diffuser.

A third embodiment of an elongate illuminator is schematically illustrated in cross section in FIG. 25. In this embodiment, the planar elongate translucent diffuser 132 is replaced by a curved elongate reflective diffuser 132" having an elongate concave face disposed toward both the elongate secondary light source 134 and the elongate beam splitter 126. The light emitting by the secondary elongate light source 134 is received, diffused and reflected by the curved diffuser 132" toward the beam splitter 126. The beam splitter 126, in turn, reflects the diffused light along the observation plane for filling the elongate observation window with secondary diffused light. This configuration provides an increased range of incident angles for the diffused light provided along the observation plane while, at the same time, reduces the required height of the illumination device above the object being viewed.

In this embodiment, panel 142 and the two diffusers 132", 123 are arranged such that light emitting from the secondary elongate light source 134 is prevented from directly illuminating the desired portion or strip 127 of the object 120 being observed. Thus no direct nondiffuse illumination of the object can occur and only uniform diffuse illumination of the desired portion or strip 127 of the object 120 to be observed is ensured.

When the elongated illumination device is incorporated into a scanner, photocopier machine with a light, the illumination device is fixedly secured to a camera 12' and forms an integrated unit 160. The camera 12' provides an input to a computer 150 via suitable wiring or cabling. The computer 150 is also connected, via suitable wiring or cabling, to a scanning or conveying apparatus or means 152 which conveys the integrated unit 160 relative to the object to be observed, i.e. the image remains stationary, as shown in FIG. 25. Alternatively, the object can be moved relative to integrated unit 160 by the scanning or conveying apparatus or means 152. The computer 150 then transmits, via suitable wiring or cabling, the sensed image to a reproducing device 154, such as a printer, a thermal imaging device or the like where a reproduction of the observed image is outputted as a reproduction 156. Alternatively, the sensed image may be send to some other device where the sensed image is further processed in some fashion, e.g. the sensed image is compared to a test image.

It is to be appreciated that the relative movement between the illumination device and the object to be observed can be achieved in the variety of different ways. The combination of the elongated diffuse illumination device, the computer, the camera and the conveying apparatus are incorporated into a combined system 162 for one of inspection and reproduction of the object to be observed.

Since certain changes may be made in the above described illumination device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

I claim:

1. An elongate diffuse illumination device for uniformly illuminating a desired elongate linear portion of an object when observed along an observing plane extending transversely of an object observing location, said diffuse lighting device comprising:

at least one elongate surface, for supplying diffused light, being located adjacent an elongate opening through which the observing plane passes, said surface being arranged to supply primary diffused light to provide said uniform illumination of the desired linear portion of the object when placed at the observing location and viewed along said observing plane, except for portion of the object effected by the elongate opening;

a source for producing secondary diffused light to illuminate the desired portion of the object effected by the elongate opening; and an elongate partially reflective mirror for supplying said secondary diffused light along the observing plane to uniformly illuminate the elongate portion of the object effected by the opening to produce, when primary diffused light simultaneously illuminates said elongate surface, said uniform illumination of the desired portion of the object when viewed along the observing plane.

2. An elongate diffuse illumination device according to claim 1 wherein said elongate surface comprises a pair of spaced apart elongate primary diffusers and a pair of elongate primary light sources which cooperate with said elongate primary diffusers to uniformly illuminate, with diffused light, the desired portion of the object except for a portion of the object effected by the elongate opening when viewed along the observing plane, and said elongate mirror is positioned along the observing plane, at a location spaced from both the desired portion of the object and the elongate opening, so as to reflect said secondary diffused light along the observing plane toward the desired portion of the object and allow light reflected by the desired portion of the object to pass through said elongate mirror to be viewed by an observation device, and said diffuse lighting device prevents said secondary diffused light from directly illuminating, during use, the desired portion of the object.

3. An elongate diffuse illumination device according to claim 2 wherein a mechanism is further provided for controlling illumination characteristics of at least one of said primary diffused light and said secondary diffused light whereby light from said primary diffused light reflected by the desired portion of the object to said mirror will be substantially identical in intensity and character to said secondary diffused light reflected by the desired portion of the object to said mirror so that uniform illumination of the desired portion of the object, when viewed along the observing plane, is facilitated.

4. An elongate diffuse illumination device according to claim 2 wherein said elongate diffuser comprises an elongate translucent envelope at least partially surrounding the desired portion of the object, said elongate translucent envelope has elongate outer and inner surfaces, and said primary light source directly and uniformly illuminates the outer surface of said translucent envelope wherein, during use, diffused light is emitted by the inner surface of said translucent envelope to the desired portion of the object.

5. An elongate diffuse illumination device according to claim 1 wherein said source for producing said secondary diffused light comprises an elongate secondary light diffuser positioned between said elongate mirror and a secondary light source for providing said secondary diffused light.

6. An elongate diffuse illumination device according to claim 5 wherein said primary light source and said secondary light source each comprise at least one of an elongate lamp, an elongate array of lamps, an elongate array of diodes, an elongate array of optical fibers, an elongate LED, an elongate array of LEDs and an elongate fluorescent light.

7. An elongate diffuse illumination device according to claim 1, further comprising an attachment mechanism for attaching said elongate diffuse illumination device to an observation device so that said observation device is positioned to receive light which is reflected from the desired portion of the object along the observing plane toward said elongate mirror; and a scanning mechanism for moving one of said observation device and said object relative to the other to scan the desired portion of the object.

8. An elongate diffuse illumination device according to claim 1 wherein said elongate mirror is positioned between an elongate light absorbing member and said source of said secondary diffused light mirror.

9. An elongated diffuse illumination device according to claim 1, in combination with an inspection camera, a computer and a conveying apparatus for moving one of said elongate diffuse illumination device and the object to be observed relative to one another, and said computer is connected with said camera and said conveying apparatus for sensing and outputting a sensed image of the object being observed.

10. An elongated diffuse illumination device according to claim 9, wherein the combination of said elongated diffuse illumination device, said computer, said camera and said conveying apparatus are incorporated into a system for one of inspection and reproduction of the object to be observed.

11. A method for uniformly illuminating, via a elongate diffuse illumination device, a desired portion of an object when observed along an observing plane extending transversely of an object observing location, said method comprising the steps of:

providing an elongate opening adjacent at least one elongate surface for supplying light, and passing the observing plane through said elongate opening;

arranging said at least one elongate surface to supply primary diffused light to provide said uniform illumination of the desired portion of the object when placed at the observing location and viewed along said observing plane, except for a portion of the object effected by the elongate opening;

providing a source of secondary diffused light to illuminate the desired portion of the object; and supplying said secondary diffused light, via a partially reflective elongate mirror, along the observing plane to uniformly illuminate the portion of the object effected by the opening to produce, when primary diffused light simultaneously illuminates said elongate surface, said uniform illumination of the desired portion of the object when viewed along the observing plane.

12. A method according to claim 11 further comprising the steps of using a pair of spaced apart elongate primary diffusers as said at least one elongate surface and directing an elongate primary light source at each of said pair of elongate primary diffusers to uniformly illuminate, with diffused light, the desired portion of the object except for the portion of the object effected by the elongate opening when viewed along the observing plane, and positioning said elongate mirror along the observing plane at a location spaced from both the desired portion of the object and the elongate opening, so as to reflect said secondary diffused light, via said elongate mirror, along the observing plane toward the desired portion of the object and allow light reflected by the desired portion of the object to pass through said elongate mirror to be viewed by an observation device, and preventing said secondary diffused light from directly illuminating, during use, the desired portion of the object.

13. A method according to claim 12 further comprising the steps of controlling illumination characteristics of at least one of said primary diffused light and said secondary diffused light via an illumination control mechanism whereby said primary diffused light, reflected by the desired portion of the object to said elongate mirror, will be substantially identical in intensity and character to said secondary diffused light reflected by the desired portion of the object to said elongate mirror so that uniform illumination of the desired portion of the object, when viewed along the observing plane, is facilitated.

14. A method according to claim 12 further comprising the steps of providing said pair of spaced apart elongate primary diffusers with elongate outer surfaces and elongate inner surfaces, and illuminating the elongate outer surfaces of said pair of spaced apart elongate primary diffusers with said elongate primary light source thereby emitting diffused light toward the desired linear portion of the object via the elongate inner surfaces of said pair of spaced apart elongate primary diffusers.

15. A method according to claim 12 further comprising the step of positioning said elongate mirror between an elongate light absorbing member and said source of said secondary diffused light for absorbing non-reflected light which passes through said elongate mirror.

16. A method according to claim 12 further comprising the steps of combing said elongated diffuse illumination device with a camera and connecting the camera to a computer via wiring; moving one of said elongate diffuse illumination device and the object to be observed relative to the other, and sensing and outputting a sensed image of the object being observed via said computer.

17. A method according to claim 16 further comprising the steps of incorporating said elongated illumination device, said computer, said camera and said conveying apparatus into a system; and reproducing an image of the object to be observed via said system.

18. A method according to claim 16 further comprising the steps of incorporating said elongated diffuse illumination device, said computer, said camera and said conveying apparatus into a system; and inspecting the object to be observed via said system.

19. A method according to claim 11 further comprising the step of positioning an elongate secondary light diffuser between said elongate mirror and an elongate secondary light source.

20. A method according to claim 11 further comprising the step attaching said elongate diffused illumination device to an observation device so that the observation device is positioned to receive light which is reflected from the desired portion of the object along the observing plane toward said elongate mirror; and moving one of the object and the observation device relative to the other to scan the desired portion of the object illuminated by the elongate diffuse illumination device and viewed by said observation device.

* * * * *